United States Patent [19]

Irick, Jr. et al.

[11] Patent Number: 5,286,903
[45] Date of Patent: Feb. 15, 1994

[54] PROCESS FOR THE PREPARATION OF CYCLOHEXANEDICARBOXYLIC ACIDS

[75] Inventors: Gether Irick, Jr., Gray; Michael Bellas, Kingsport; Leslie S. LaForce, Jonesborough, all of Tenn.

[73] Assignee: Eastman Kodak Company, Rochester, N.Y.

[21] Appl. No.: 993,537

[22] Filed: Dec. 21, 1992

[51] Int. Cl.$^5$ .............................................. C07C 61/09
[52] U.S. Cl. ............................................................ 562/509
[58] Field of Search ............................................. 562/509

[56] References Cited

U.S. PATENT DOCUMENTS 4,918,226  4/1990  Pruett .................................. 562/509

OTHER PUBLICATIONS

Migrdichian, "Organic Synthesis," vol. 1, pp. 336–339 and 353–358 (1957).

Primary Examiner—Michael L. Shippen
Attorney, Agent, or Firm—J. Frederick Thomsen; William P. Heath, Jr.

[57] ABSTRACT

Disclosed are processes for the preparation of cyclohexanedicarboxylic acids by the non-catalytic hydrolysis or acidolysis of dialkyl cyclohexanedicarboxylate esters. The processes provide a means for converting dialkyl cyclohexanedicarboxylate esters to cyclohexanedicarboxylic acids without the co-production of solid by-products which present disposal problems.

2 Claims, No Drawings

PROCESS FOR THE PREPARATION OF CYCLOHEXANEDICARBOXYLIC ACIDS

This invention pertains to processes for the preparation of cyclohexanedicarboxylic acids by the non-catalytic hydrolysis or acidolysis of dialkyl cyclohexanedicarboxylate esters. The processes provide a means for converting dialkyl cyclohexanedicarboxylate esters to cyclohexanedicarboxylic acids without the co-production of solid by-products which present disposal problems.

While the hydrolysis of esters to carboxylic acids using both acid and base catalysts is well-known, these processes give products from which the catalyst and/or their reaction products must be removed. This is undesirable from both cost and environmental viewpoints. It is known to produce 1,4-cyclohexanedicarboxylic acid by the sulfuric acid catalyzed hydrolysis of dimethyl 1,4-cyclohexanedicarboxylate. This process requires the use of a toxic acid and requires that it be removed from the product and neutralized. The process thus produces and requires the disposal of metal sulfates.

Another means for producing 1,4-cyclohexanedicarboxylic acid comprises the hydrogenation of the sodium salt of terephthalic acid followed by acidification of the resulting disodium 1,4-cyclohexanedicarboxylate with sulfuric acid. Again, the process produces and requires the disposal of a metal sulfate.

The present invention provides a means for producing cyclohexanedicarboxylic acids at commercially acceptable rates without the need for a catalyst and without the co-production of solid products which require disposal. In accordance with the present invention, cyclohexanedicarboxylic acids are prepared by the non-catalytic process comprising heating a mixture comprising (i) a dialkyl cyclohexanedicarboxylate and (ii) water, a carboxylic acid containing 2 to about 6 carbon atoms, or a mixture thereof at about 200° to 350° C. The co-product of the process is an alkanol and/or a carboxylic acid ester of the alkanol, depending on whether water and/or a carboxylic acid containing 2 to about 6 carbon atoms are used.

Since the non-catalytic process of the invention is carried out at temperatures well above the boiling points of both water and carboxylic acids of 2 to about 6 carbon atoms, it must be carried out in pressure vessels under atogenous pressures. When operating the hydrolysis process wherein a dialkyl cyclohexanedicarboxylate is heated in the presence of water, the temperature employed preferably is about 220° to 280° C. When the process is carried out as an acidolysis reaction wherein a dialkyl cyclohexanedicarboxylate is heated in the presence of a carboxylic acid of 2 to about 6 carbon atoms, the temperature employed normally should be at least 235° C. and preferably is in the range of about 250° to 300° C.

The amount of water and/or carboxylic acid employed in the practice of the invention normally is at least 2 moles of water and/or carboxylic acid per mole of dialkyl cyclohexanedicarboxylate but preferably is in the range of about 8 to 20 moles water and/or carboxylic acid per mole of dialkyl cyclohexanedicarboxylate. The alkyl residues of the dialkyl cyclohexanedicarboxylate reactants can be alkyl of up to about 4 carbon atoms with methyl being especially preferred. The cyclohexanedicarboxylate ester reactants preferably are selected from 1,3- and 1,4-cyclohexanedicarboxylates.

The carboxylic acids useful in the practice of the invention include both mono- and di-carboxylic, aliphatic acids containing 2 to about 6 carbon atoms. Examples of such acids are acetic, propionic, butyric, succinic, glutaric, adipic, and similar acids. Acetic acid is particularly preferred.

Since the products from the hydrolysis and acidolysis reactions generally are insoluble in the reaction mixture at temperatures below about 120° C., no solvent in the true sense is necessary. However, an excess of water or the carboxylic acid above the preferred range of 8 to 20 moles water/acid per mole of dialkyl cyclohexanedicarboxylate may be desirable under certain processing conditions. For example, if the process is run in a continuous manner, an excess of water of carboxylic acid may be necessary to permit the product slurry to be pumped from the reaction zone to the filtration/centrifugation area. Optionally, a solvent which is inert to the hydrolysis may be used for the same purpose. The composition of the inert solvent is not critical, but typical solvents include diphenyl ether, diphenyl ether/biphenyl mixtures and toluene.

The hydrolysis and acidolysis processes of the present invention may be operated as a batch, semicontinuous of continuous process using suitable pressure equipment. For example, in continuous operation, water and the dialkyl cyclohexanedicarboxylate reactant are fed continuously to a reactor, methanol co-product is removed continuously as a vapor, and the crude product is removed continuously as a slurry of the cyclohexanedicarboxylic acid product. The product is separated from the reaction slurry by conventional liquid/solid separation techniques such as filtration or centrifugation. The filtrate or centrate containing small amounts of reactant, partially converted reactant, $C_2-C_6$ aliphatic carboxylic acid and/or water, and other organic materials can be returned to the reactor. Removal of the methanol or methyl carboxylate, while not essential, will increase somewhat the rate at which the hydrolysis or acidolysis occurs.

The process of the present invention is non-catalytic by which we mean that neither a strong acid or base is utilized to effect the hydrolysis nor is any material employed to catalyze the acidolysis (or transesterification) reaction. Thus, in the batch operation of the hydrolysis reaction, the process starts of at neutral pH and becomes acidic due to the formation of hydrolysis products such as the monoalkyl cyclohexanedicarboxylate and the cyclohexanedicarboxylic acid product. In the acidolysis of dialkyl cyclohexanedicarboxylates, no acid having a pK of less than 3.0 is required for the process to operate satisfactorily and therefore the process is carried out in the absence cf an acid having a pK of less than 3.0. For example the pK values for acetic, adipic, isophthalic and terephthalic acids are 4.75, 4.43, 3.54 and 3.51, respectively.

The process provided by our invention is further illustrated by the following examples.

EXAMPLE 1

A mixture of dimethyl 1,4-cyclohexanedicarboxylate (20 g) and acetic acid (60 g) was placed in a 1 inch by 10 inch Pyrex glass autoclave liner fitted in a magnetically stirred Hastelloy autoclave. The mixture was heated at 250° C. for 12 hours, cooled and filtered to recover a white solid product. The product had an acid number of 663 (determined by titration with potassium hydroxide solution) corresponding to the acid number of 1,4- cyclohexanedicarboxylic acid. This represents essentially 100% acidolysis of the dimethyl 1,4-cyclohexanedicarboxylate to 1,4-cyclohexanedicarboxylic acid.

EXAMPLE 2

Example 1 was repeated using a temperature of 300° C. The solid recovered had an acid number of 660 representing 99.5% acidolysis of the starting material.

EXAMPLE 3

Example 1 was repeated with the addition of 1.9 g water. The solid recovered had an acid number of 562.3 representing 84.1% acidolysis of the dimethyl 1,4-cyclohexanedicarboxylate to 1,4-cyclohexanedicarboxylic acid.

EXAMPLE 4

Example 1 was repeated except that dimethyl 1,3-cyclohexanedicarboxylate was the ester reactant. 99% of the ester reactant was converted to a mixture of monomethyl 1,3-cyclohexanedicarboxylate and 1,3-cyclohexanedicarboxylic acid based on the depletion of the ester reactant as determined by gas chromatographic analysis of the filtrate using diphenyl ether as the internal standard.

EXAMPLE 5

A mixture of dimethyl 1,4-cyclohexanedicarboxylate (40 g) and water (36 g) was placed in a 1 inch by 10 inch Pyrex glass autoclave liner fitted in a magnetically stirred Hastelloy autoclave. The mixture was stirred at 220° C. for 5 hours, cooled and filtered to recover a white solid product. The product had an acid number of 366 (determined by titration with potassium hydroxide solution) which represents 55.2% hydrolysis of the dimethyl 1,4-cyclohexanedicarboxylate to 1,4-cyclohexanedicarboxylic acid.

EXAMPLE 6

Example 5 was repeated using a temperature of 280° C. and a heating period of 10 hours. The solid recovered had an acid number of 435 representing 65.6% acidolysis of the dimethyl 1,4-cyclohexanedicarboxylate to 1,4-cyclohexanedicarboxylic acid.

EXAMPLE 7

Repeating Example 5 at a temperature of 200° C. gave 73% hydrolysis of the dimethyl 1,4-cyclohexanedicarboxylate.

EXAMPLE 8

Example 5 was repeated using dimethyl 1,3-cyclohexanedicarboxylate as the dialkyl cyclohexanedicarboxylate reactant. 61.5% of the ester reactant was converted to a mixture of monomethyl 1,3-oyclohexanedicarboxylate and 1,3-cyclohexanedicarboxylic acid based on the depletion of the ester reactant as determined by gas chromatographic analysis of the filtrate using diphenyl ether as the internal standard.

The invention has been described in detail with particular reference to preferred embodiments thereof, but it will be understood that variations and modifications can be effected within the spirit and scope of the invention.

We claim:

1. A non-catalytic process for the preparation of a cyclohexanedicarboxylic acid which comprises heating a mixture comprising (i) a dialklyl cyclohexanedicarboxylate and (ii) a carboxylic acid containing 2 to about 6 carbon atoms at about 250° to 300° C., wherein the alkyl residues of the dialkyl cyclohexanedicarboxylate contain up to about 4 carbon atoms.

2. Process according to claim 1 wherein the dialkyl cyclohexanedicarboxylate is dimethyl 1,3-cyclohexanedicarboxylate or dimethyl 1,4-cyclohexanedicarboxylate and the carboxylic acid is acetic acid.

* * * * *